US005861501A

United States Patent [19]

Benseler et al.

[11] Patent Number: 5,861,501

[45] Date of Patent: Jan. 19, 1999

[54] CAPPED SYNTHETIC RNA, ANALOGS, AND APTAMERS

[75] Inventors: Fritz Benseler, Goettingen, Germany; James L. Cole, Doylestown, Pa.; David B. Olsen, Lansdale, Pa.; Lawrence C. Kuo, Solebury, Pa.

[73] Assignee: Merck & Co., Inc., Rahway, N.J.

[21] Appl. No.: 807,104

[22] Filed: Feb. 4, 1997

Related U.S. Application Data

[62] Division of Ser. No. 480,068, Jun. 7, 1995.

[51] Int. Cl.$^6$ .................. C07H 21/02

[52] U.S. Cl. .................. 536/24.5; 536/23.1

[58] Field of Search .................. 514/44; 536/24.5, 536/23.1

[56] References Cited

FOREIGN PATENT DOCUMENTS

| | | |
|---|---|---|
| WO 90/15065 | 5/1990 | WIPO . |
| WO 92/14843 | 2/1992 | WIPO . |

OTHER PUBLICATIONS

Chung et al., Proc. Natl. Acad. Sci. USA 91:2372–2376, Mar. 1994.

Ludwig, et al., "Rapid and Efficient Synthesis of Nucleoside 5'–O–(1–Thiophosphates) 5'–Triphosphates . . . ", J. Org. Chem., vol. 54, pp. 631–635, 1989.

Hay, "Bone Disease in Liver Transplant Recipients", Advances in Liver Transplantstion, vol. 22, pp. 337–349, Jun. 1993.

Stull, et al., "Antigen, Ribozyme and Aptamer Nucleic Acid Drugs: Progress and Prospects", Pharmaceutical Research, vol. 12, No. 4, 1995.

Horn, et al., "A Chemical 5'–Phosphorylation of Oligodeoxyribonucleotides That Can Be Monitored by Trityl . . . ", Tetrahedron Letters, vol. 27, No. 29, pp. 4705–4708, 1986.

Beuacage, et al., "Deoxynucleoside Phosphoramidites–A New Class of Key Intermediates for . . . ", Tetrahedron Letters, vol. 22, No. 20, pp. 1859–1862, 1981.

Moffatt, "A General Synthesis of Nucleoside–5' Triphosphates", Canadian J. of Chem., vol. 42, pp. 599–604, 1964.

Uhlmann, et al., "Chemical 5'–Phosphorylation of Oligonucleotides Valuable in Automated DNA Synthesis", Tet. Letters, vol. 27, No. 9, pp. 1023–1026, 1986.

Sinha, et al., "Polymer Support Oligonucleotide Synthesis XVI1: Synthesis of Oligonucleotides . . . ", Nucleosides and Nucleotides, vol. 3, No. 2, pp. 157–171, 1984.

Iwase, et al., "Molecular design of a eukaryotic messenger RNA and its chemical synthesis", Nucleic Acids Research, vol. 20, No. 7, pp. 1643–1648.

Guar, et al., "Novel Solid Phase Synthesis of 2'–O–Methylribonucleoside 5'–Triphosphates and their G–Thio . . . ", Tet. Letters, vol. 33, No. 23, pp. 3301–3304, 1992.

Pieken, et al., "Kinetic Characterization of Ribonuclease–Resistant 2'–Modified Hammerhead Ribozymes", Science, vol. 253, pp. 314–317, 1991.

Heidenreich, et al., "High Activity and Stability of Hammerhead Ribozymes Containing 2'–Modified Pyrimidine . . . ", J. Biol. Chem., vol. 269, No. 3, pp. 2131–2138, 1994.

Tsuchl, et al., "Importance of Exocyclic Base Functional Groups of Central Core Guanoosines for Hammerhead . . . ", Biochemistry, vol. 32, pp. 11658–11668, 1993.

Horn, et al., "Laboratory Methods: A Chemical 5'–Phosphorylation of Oligodeoxyribonucleotides . . . ", DNA, vol. 5, No. 5, pp. 421–426, 1986.

Plotch, et al., "A Unique Cap (m7GpppXm)–Dependent Influenza Virion Endonuclease Cleaves Capped RNAs . . . ", Cell, vol. 23, pp. 847–858, Mar. 1981.

Olsen, et al., "Study of Hammerhead Ribozyme Containing 2'–Modified Adenosine Residues", Biochemistry, vol. 30, pp. 9735–9741, 1991.

*Primary Examiner*—Stephanie W. Zitomer
*Attorney, Agent, or Firm*—Michael D. Yablonsky; Jack L. Tribble; JoAnne M. Giesser

[57] ABSTRACT

A method is provided for making synthetic capped RNAs. These compounds serve as substrates for the virally encoded endonuclease associated with influenza virus. We are able to assay for this unique and specific viral activity of cleavage of a capped RNA in vitro. Therefore, screening of inhibitors of this activity is possible. In addition, short non-extendible (due to their length or because of the modification of the 3'-end of the oligo, i.e. 3'-dA) RNAs are potent inhibitors of the cleavage of capped RNAs by influenza endonuclease. Finally, these compounds may be used to investigate viral and cellular mechanisms of transcription/translation or mRNA maturation.

2 Claims, 5 Drawing Sheets

IA

II A

III A

IV A

V A

VI A

VII A

CAPPED SYNTHETIC RNA, ANALOGS, AND APTAMERS

This is a division of application Ser. No. 08/480,068 filed Jun. 7, 1995.

DESCRIPTION OF THE INVENTION

This invention is directed towards synthetic ribonucleic acid (RNA), analogs, and aptamers which have been capped in vitro and to methods of making them.

BACKGROUND OF THE INVENTION

Most viral and cellular mRNA molecules contain a 5'-methylated cap structure. The presence of such a structure is important for mRNA maturation, initiation of translation and protects the mRNA against degradation by various RNases present in the cell. There are various types of RNA caps known. The general structure of a capped RNA can be designated as $m^7G(5')ppp(5')Pu$, (where Pu, the penultimate base, is typically a purine nucleoside).

In the so-called "Cap 0", the penultimate base is unmodified. "Cap 0" is found commonly in yeast, the majority of slime molds, and in plant viruses.

The penultimate base of "Cap 1" containing mRNAs is 2'-O-methylated and can be designated $m^7G(5')ppp(5')Pu$ (2'-OMe). It is formed as a result of the action of a 2'-O-methyltransferase activity. Many mRNAs from animal viruses have a "Cap 1" structure. The presence of the 2'-O-methyl group stabilizes the first 3',5'-phosphodiester linkage of "Cap 1"-containing mRNAs against RNase T2 cleavage.

Messenger RNAs having a "Cap 2" structure have two 2'-O-methyl groups: one on the penultimate base and the second on the next base 3'to the penultimate base [$m^7G(5')ppp(5')Pu(2'OMe)X(2'OMe)$]. This is found in silk fibroin mRNA, vesicular stomatitis virus mRNA and other cellular and viral mRNAs. The presence of caps and their type can be readily determined by those skilled in the art; one method includes treating the mRNA with T2 RNase and alkaline phosphatase and analyzing the digest by DEAE-cellulose chromatography.

Influenza virus endonuclease uses a capped RNA as its substrate. Detailed enzymological studies of this endonuclease have been hindered in the past because it is quite difficult to synthesize capped RNAs of desired purity and/or capped RNAs which contain analogs. Further, in view of the synthesis problems, it has been impossible to identify well defined short capped RNA or RNA analog molecules which could be used as substrates or inhibitors of influenza endonuclease, and which could be potential therapeutic and/or prophylactic agents.

Aptamers are single-stranded or double-stranded nucleic acids which are capable of binding proteins or other small molecules. Aptamers which have therapeutic value would most likely bind proteins involved in the regulation and expression of genes, such as transcription factors. The presence of the aptamer would act as a sink for the protein factors, preventing the factors from carrying out their normal functions and presumably modulating the expression of genes dependent upon the activity of this protein. To date, only a few aptamers are known. It would be desirable to identify novel aptamers active against enzymes such as influenza endonuclease and to be able to easily sythesize them.

In the past, capped RNA molecules have been made in vitro by "runoff" transcription. There are two routes to obtaining a capped RNA by this procedure. The first is to carry out an RNA synthesis reaction using a DNA template and an RNA polymerase, such as T7 RNA polymerase, in the presence of a capped dinucleotide such as $m^7G(5')ppp(5')G$. A second methodology carries out the runoff transcription reaction and the resulting RNA is then treated with an enzyme, guanylyltransferase, which "caps" the RNA.

These two methods suffer from several problems. First, while both methods are generally efficient for producing long polyribonucleic acids (i.e., more than approximately 100 bases), they do not generally work well for shorter nucleotides (i.e., less than about 40 bases). There are also problems with maintaining fidelity of the sequence of the resulting oligoribonucleotide, as transcriptional errors cannot be ruled out during "runoff" transcription. The major disadvantage of the first method is that a low percentage of the RNAs produced will contain the Cap. Further, the RNA product will have a Cap 0 structure, and certain enzymes such as influenza endonuclease requires a Cap 1 structure to bind. Secondly, 2'-O-methylation is generally inefficient and the extent of methylation cannot be ascertained in a simple manner.

Another major limitation of this methodology is that the vast majority of nucleoside (or non-nucleoside) analogs cannot be incorporated into the RNA in a site specific manner. Furthermore, there is difficulty in synthesizing RNAs containing such analogs because the analogs are not utilized as substrates by the polymerase. Similarly, in the case of RNA analogs which contain backbone modifications such as phosphorothioates or methylphosphonates, usually only one of the corresponding diastereoisomers is recognized as a substrate by the polymerase.

It would be desirable to have a simplified, efficient method for producing short capped unmodified or modified RNAs.

DETAILED DESCRIPTION OF THE INVENTION

This invention is directed to a method for producing capped ribonucleic acid molecules, analogs, and aptamers comprising the steps of: a) reacting an RNA or RNA analog oligonucleotide with a phosphate addition agent to form an RNA or RNA analog mono-, di- or triphosphate; and b) capping the RNA or RNA analog mono-, di- or triphosphate.

This invention specifically is directed to a method of producing capped RNA oligonucleotides, capped RNA analog oligonucleotides, and aptamers comprising the steps of: a) reacting an RNA oligoribonucleotide or RNA analog oligonucleotide with a phosphate addition agent to form a first intermediate; b) reacting the first intermediate with a phosphate analog to form a cyclic triphosphate intermediate or a diphosphate intermediate; c) oxidizing and hydrolyzing the cyclic triphosphate intermediate or diphosphate intermediate to result in a triphosphate or diphosphate; and d) capping the diphosphate or triphosphate to form a capped RNA, capped RNA analog, or aptamer.

This invention further relates to particular capped RNAs and capped RNA analogs which may be produced by the process of this invention. These molecules are substrates for influenza endonuclease, and as such can be used to gain new insights as to the mechanism of the endonucleases. This invention further relates to specific aptamers which are substrate inhibitors of influenza endonuclease, an enzyme which is critical to the replication and resulting infectivity of the influenza virus. Thus, another aspect of this invention is a method of preventing or treating influenza in an animal, including humans, which is susceptible to infection by the influenza virus by administering an effective amount of an influenza endonuclease aptamer.

As used throughout the specification and claims, the following definitions apply:

"RNA analog": a polymeric molecule, which in addition to containing ribonucleosides as its units, also contains at least one of the following: 2'-deoxy, 2'-halo, 2'-amino (not substituted or mono- or disubstituted), 2'-mono-, di- or tri-halomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$alkyl groups, abasic linkers, 3'-deoxy-adenosine as well as other available "chain terminator" or "non-extendible" analogs (at the 3'-end of the RNA), or labels such as $^{32}P$, $^{33}P$ and the like. All of the foregoing may be incorporated during the synthesis step.

"Aptamer": a single- or double- stranded nucleic acid which is capable of binding to a protein or other molecule, and thereby disturbing the protein's or other molecule's function.

"Influenza endonuclease aptamer": a single- or double-stranded nucleic acid which binds to influenza endonuclease and disturbs its function.

In preferred embodiments of this invention, the RNA or its analog is synthesized on a solid support column, using conventional techniques such as those described by Beuacage et al 1981 Tetrahedr. Letters 22:1859–1862 and Sinha et al, 1984 Nucleosides and Nucleotides 3:157–171, both of which are incorporated by reference. The final DMT-group is removed from the resulting RNA or analog. Alternately, if large-scale synthesis is used, the RNA can be made by scale-up of the solid support method or the RNA can be made by using solution phase techniques, particularly if the desired end-product is a relatively short oligonucleotide. Regardless of the method used to synthesize the RNA or analog, the starting material for the process of this invention will be a 5'-non-tritylated RNA oligoribo-nucleotide or analog of the desired primary structure, which preferably may have protected bases, and which is preferably bound to a solid-support. Any conventionally used protecting groups may be used. Typically $N^6$-benzoyl is used for adenine, $N^4$-benzoyl for cytosine, $N^2$-isobutyryl for guanine and $N^2$-benzoyl for 2-amino purine. Other useful protecting groups include phenoxyacetyl (PAC) and t-butoxyacetyl (TAC). Conveniently, the more base labile protection groups should be used for the synthesis of the RNA or analog fragment; these groups are known to those of ordinary skill in the art. Such groups may help to prevent hydrolysis of the generated tri- or diphosphates, which are generally quite stable under basic conditions, but may be subject to some hydrolysis.

Figure 4:
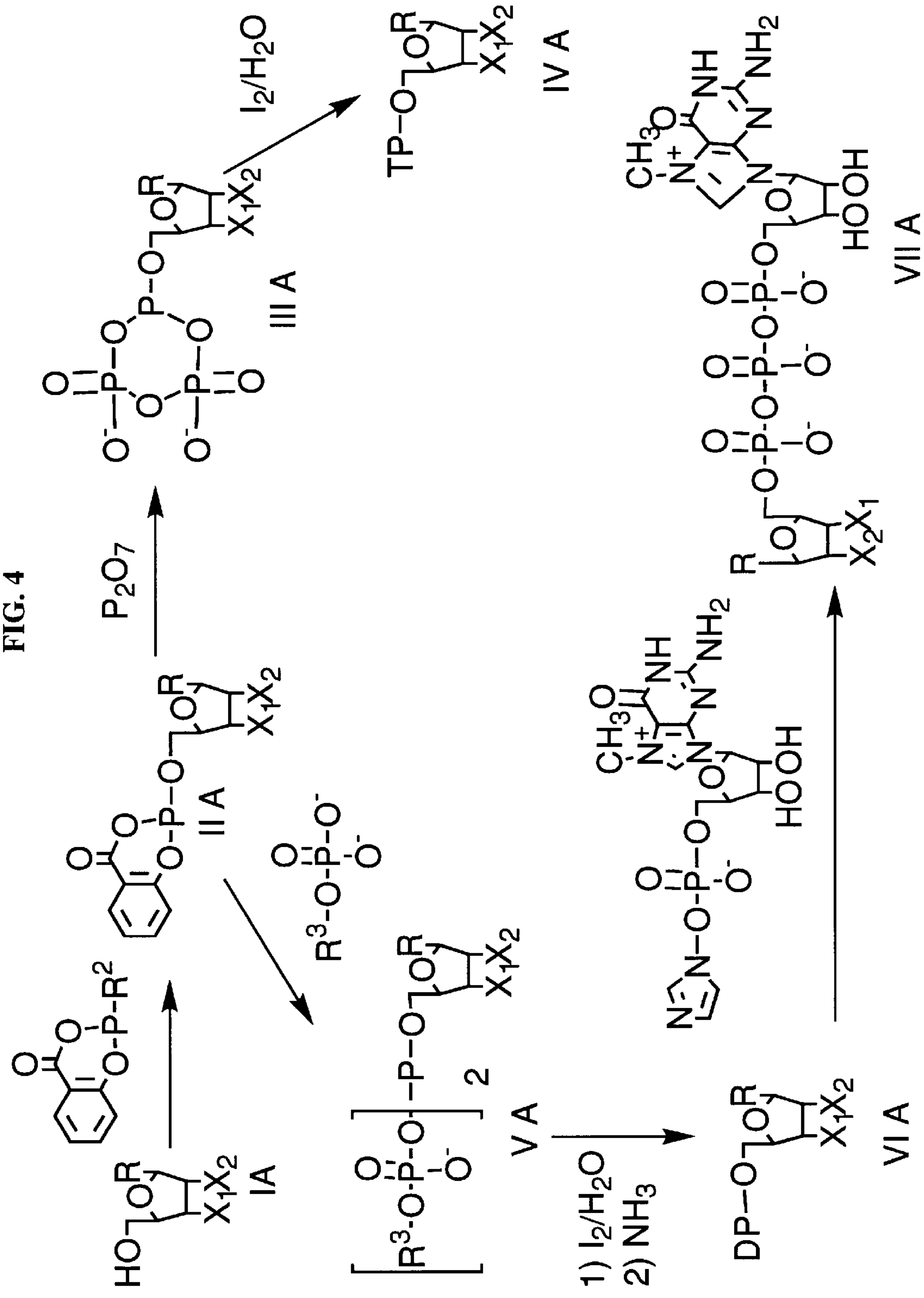
FIG. 4 shows a reaction scheme in accordance with this invention.

Referring to FIG. 4, Reaction Scheme A, compound IA, R is the penultimate base or analog; and is preferably a purine (either adenosine or guanine). X1 is a 3'-phosphotriester moiety linking the penultimate nucleoside to the next ribonucleic acid base, and X2 is 2'-O-methyl (for the synthesis of Cap 1 structures). Various types of linkers may be used. Examples of suitable linkers include (either singly or in multiply repeating units): HO—$C_3$—OH, polyethylene glycol-type linkers including tri-, tetra- or hexaethylene glycol; abasic sits such as deoxyribose or ribose; and more rigid linkers including HO—$CH_2CH_2$—$C_6H_4$—$CH_2CH_2$—OH and the like.

Next, the fully protected RNA or analog is reacted with a phosphate-addition agent. A first type of phosphate-addition agent is a phosphitylation agent which, after phosphitylation, is capable of undergoing a plurality of nucleophilic displacement reactions, and in particular at least two nucleophilic displacement reactions. This is shown in FIG. 4, Reaction Scheme A. The oxidation of the intermediates followed by hydrolysis will furnish either tri- or diphosphates depending on the nucleophile used in the displacement reactions. While any known such phosphitylating agent or agents having the described functionality may be employed, preferred phosphitylating agents have the formula

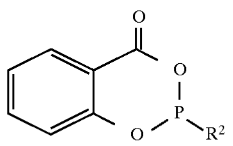

wherein $R^2$ is Cl,

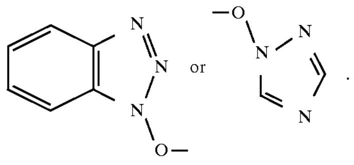

Preferably, the phosphitylation agent is 2-chloro-4H-1,3,2-benzodioxa-phosphorin-4-one, or a ring-substituted derivative of this compound. The ratio of phosphitylation agent to RNA is generally not critical, preferably it is in the range of approximately 1:1 to approximately 15:1, and is more preferably approximately 10:1. This reaction can take place at convenient temperatures, from about −20° C. to about 100° C., and more preferably at temperatures of about 20° C. to about 35° C. This reaction produces a first intermediate, designated IIA in the Reaction Scheme A.

The first intermediate formed is then reacted with a suitably prepared phosphate, pyrophosphate, salt of pyrophosphate, or an analog of the reagents. One such salt of pyrophosphate is (tri-n-butylammonium pyrophosphate). In the case of pyrophosphate, an intermediate cyclic triphosphite is formed, shown below as IIIA.

Next, the cyclic triphosphite intermediate is oxidized and hydrolyzed with an oxidation agent and water. These two reactions may take place simultaneously if the oxidizing agent is in an aqueous solution, which is shown below as IVA. Alternatively, the oxidizing and hydrolyzing may be done in separate steps. Suitable oxidizing/hydrolyzing agents include iodine in water, t-butyl hydroperoxide, di-t-butyl hydroperoxide, cumene hydroperoxide, hydrogen peroxide, and other peroxide derviatives. Further oxidizing/hydrolyzing agents include dinitrogen tetroxide, iodobenzene diacetate, tetra-n-butylammonium periodate and sulfur.

Alternatively, one could react IIA with a phosphate, of the formula

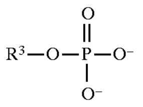

wherein $R^3$ is $-CH_2CH_2CN$,

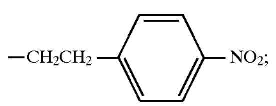

or

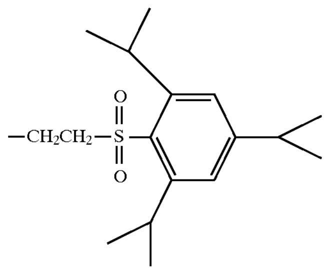

or the like. The resulting intermediate VA is then oxidized and hydrolyzed to produce the di-phosphate molecule, shown as VI A. In addition, IVA can be reacted with an appropriately activated $m^7$GMP or analog which would yield VIIA (FIG. 4).

Figure 5:
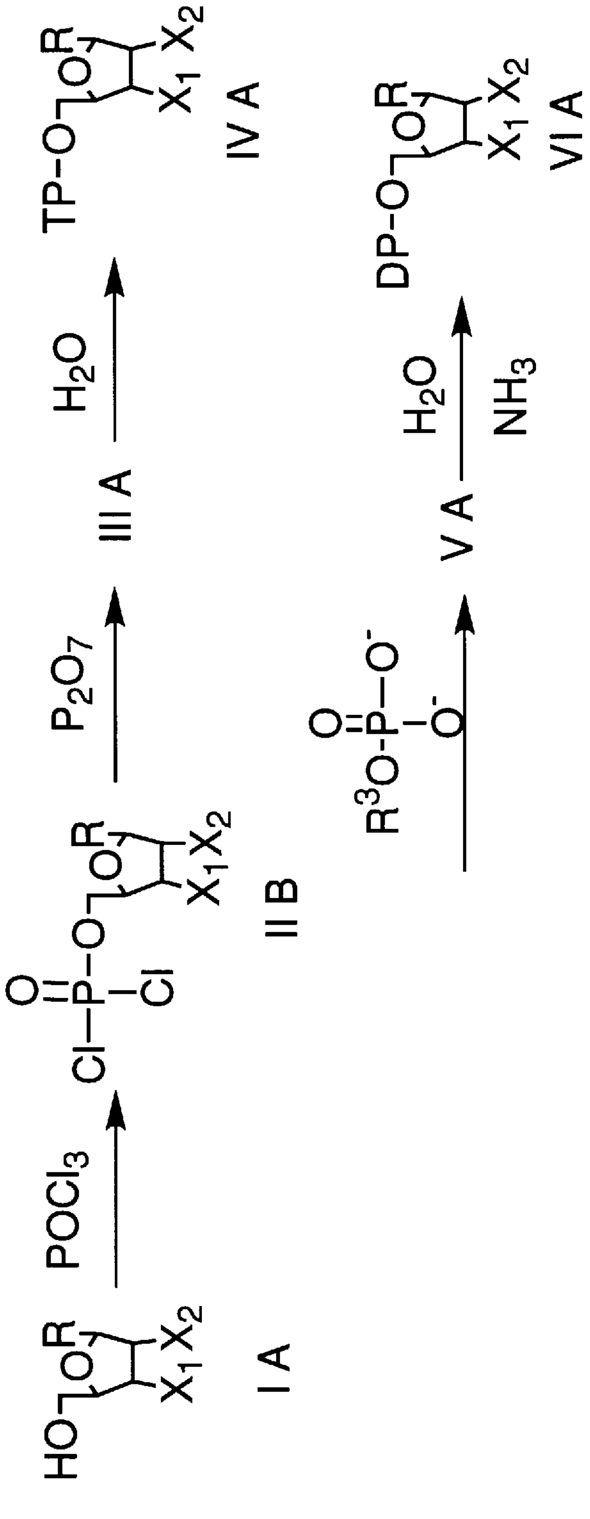
FIG. 5 shows a reaction scheme in accordance with this invention.

A second type of the phosphate-addition agent is a phosphorylation agent which, after phosphorylation, is capable of undergoing a plurality of reactions and in particular at least two subsequent reactions. Depending on the reagent participating in the reaction, either tri- or di-phosphates will be formed after neutral aqueous or basic hydrolysis of the intermediates. This is shown in FIG. 5, Reaction Scheme B. While any such phosphorylation agent may be employed, a preferred phosphorylation agent is $POCl_3$. This is reacted with the starting material to form intermediate IIB. Next, intermediate IIB may be treated similarly as in Reaction Scheme A to form the triphosphate oligonucleotide (IVA) or may be treated with a phosphate, as in Reaction Scheme A, to form the diphosphate oligonucleotide (VIA).

A third type of phosphate-addition agent is either a phosphitylafion or a phosphorylation agent, which after the reaction, can be transformed into a monophosphate monoester by adequate oxidation (when a phosphitylation agent was used) and deprotection and/or hydrolysis steps. This is diagrammed in FIG. 6, Reaction Scheme C. While any known such phosphitylation or phosphorylation agents having the described functionality may be employed, preferred phosphorylation and phosphitylation agents are $POCl_3$ and reagents described in Horn et al 1986 DNA 5(5):412–426; Uhlmann et al 1986 Tetrahed. Lett. 27(9): 1023–1026 and Horn et al, 1986 Tetrahed. Lett. 27:4705–4708, each of which is hereby incorporated by reference. Alternatively, a phosphitylation agent of the formula below may be used:

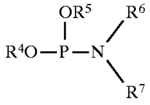

wherein $R^4$ and $R^5$ are independently selected from the group consisting of $-CH_2CH_2CN$,

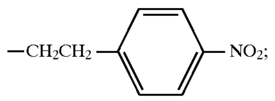

and

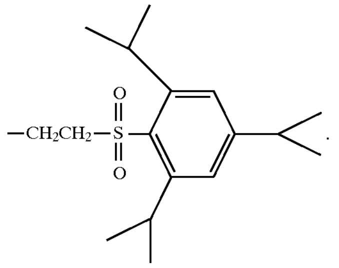

Figure 6:
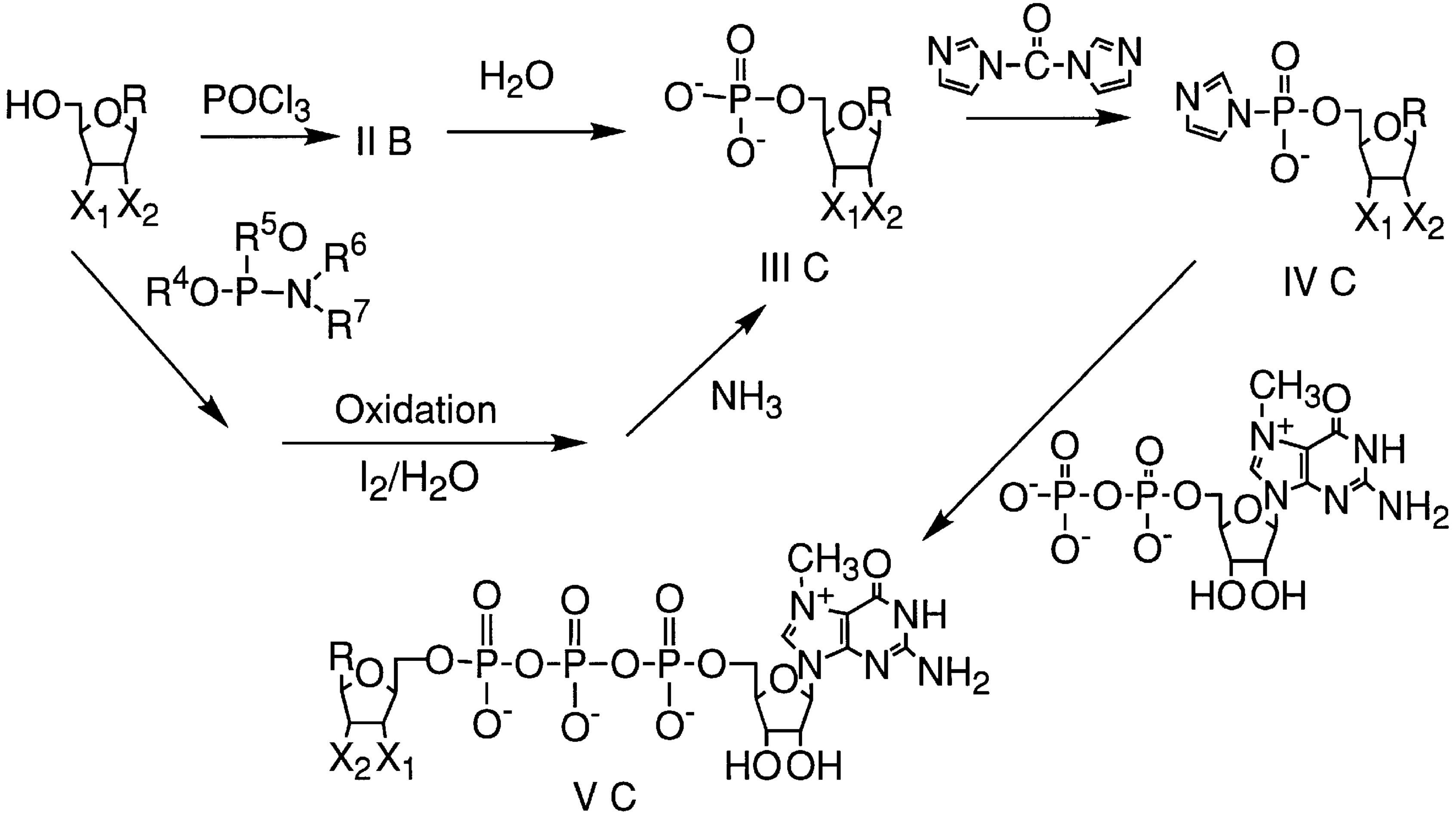
FIG. 6 shows a reaction scheme in accordance with this invention.

$R^6$ and $R^7$ are preferably $-CH(CH_3)_2$. The resulting intermediate is then oxidized and hydrolyzed to obtain IIIC. The resulting 5'-monophosphorylated oligonucleotides are transformed into di- or triphosphates or cap-like structures after activation of the monoester with reagents such as carbonyldiimidazole or a similar reagent, and a subsequent reaction with either a mono- or diphosphate, $m^7$GDP, or analogs, capped by reacting with $m^7$GDP (or analog), yielding VC, as shown in FIG. 6.

After standard RNA deblocking and purification, the resulting 5'-di- or triphosphorylated oligoribonucleic acid or analog is incubated with a capping enzyme, such as guanylyltransferase, in order to obtain the desired capped RNA. Along with the capping enzyme other reactants may be required for the reaction to occur successfully; these are known in the art. For example, for guanylyltransferase, GTP and S-adenosyl-L-methionine and a divalent cation should also be present. Alternatively, the cap could be introduced chemically, as described by R. Iwase et al, 1992, Nucl. Acids Res. 20(7):1643–1648 and Fukuoda et al, 1993 Nucleic Acids Symposia 29:25–26. For a triphosphate (TP) oligoribonucleotide, the activated RNA-TP is reacted with $m^7$G, or RNA-TP is reacted with an activated 5'-$m^7$G. For a diphosphate (DP) oligoribonucleotide, the capping can be performed by reacting activated RNA-DP with $m^7$G-MP, or by reacting the activated $m^7$G-MP with the RNA-DP. For a monphosphate (MP) oligoribonucleotide, the capping can be performed by reacting activated RNA-MP with $m^7$G-DP, or by reacting the activated $m^7$G-DP with the RNA-MP.

While the RNA or analog of this invention may have any form of cap, it is preferred that it has a Cap-1 structure, particularly if the capped oligoribonucleotide is to be used in investigating influenza endonuclease, as this particular endonuclease prefers a Cap-1 RNA as a substrate.

The capped RNA or analog of this invention may be of any length, the only limit being that of the synthesis technique employed to prepare the RNA or analog. Currently, the practical limit is approximately 50 bases, but with improvements in synthetic technology the length of the oligonucleotide is expected to increase. For purposes of this invention, it is preferred that the capped RNA or analog be less than approximately 50 bases in length, and preferably less than about 20 bases in length.

In addition, nucleoside analogs such as 2'-deoxy, 2'-halo, 2'-amino (not substituted or mono- or disubstituted), 2'-mono, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$alkyl groups, abasic linkers, 3'-deoxy-adenosine as well as other available "chain terminator" or "non-extendible" analogs (at the 3'-end of the RNA), and the like may be incorporated during the RNA synthesis. Further, various labels such as $^{32}P$ or $^{33}P$ and the like may likewise be incorporated during the synthesis, resulting in novel RNA analogs produced by this process.

The capped RNAs and analogs of this invention have numerous uses. One preferred use is as starting materials in assays measuring activity of enzymes which act on capped nucleotide substrates, as further detailed in co-pending U.S. Pat. applications Ser. Nos. 08/487,759, filed Jun. 7, 1995, now U.S. Pat. No. 5,660,989, Aug. 26, 1997 and 08/487,760, filed Jun. 7, 1995, now abandoned, and both of which are hereby incorporated by reference. For example, the influenza virus endonuclease acts on the "Cap 1" RNA structure depicted as V, above. The endonuclease then specifically cleaves the capped RNA, resulting in 5'- terminal fragments of approximately 10–15 bases in length. These capped oligonucleotides then serve as primers in viral mRNA synthesis catalyzed by the viral transcriptase. See, e.g. Plotch et al, 1989, Cell 23:847–858. Thus, one may use the capped RNA substrate to measure: a) enzyme activity as an indication of the presence of influenza endonuclease; b) for detailed mechanistic studies; c) the cleavage point of a particular enzyme; or d) whether a test substance has inhibitory activity against this enzyme. In addition, analogs of an RNA substrate may be utilized to a) investigate the requirements of a particular enzyme substrate; and b) to prepare stable RNAs such as those listed below containing 2'-fluoro groups. Another preferred use is as aptamers, especially for influenza endonuclease.

The following synthetic 19-mer RNA was produced in accordance with this invention. It is based on the 5'-region of Alfalfa Mosaic Virus (ALMV), and its novel features include the presence of a 2'-O-methyl group and a 5'-triphosphate on the penultimate nucleoside:

pppG(2'-OMe)UUUUUAUUUUUAAUUUUC-3'(SEQ. ID. NO:1)

Figure 1:
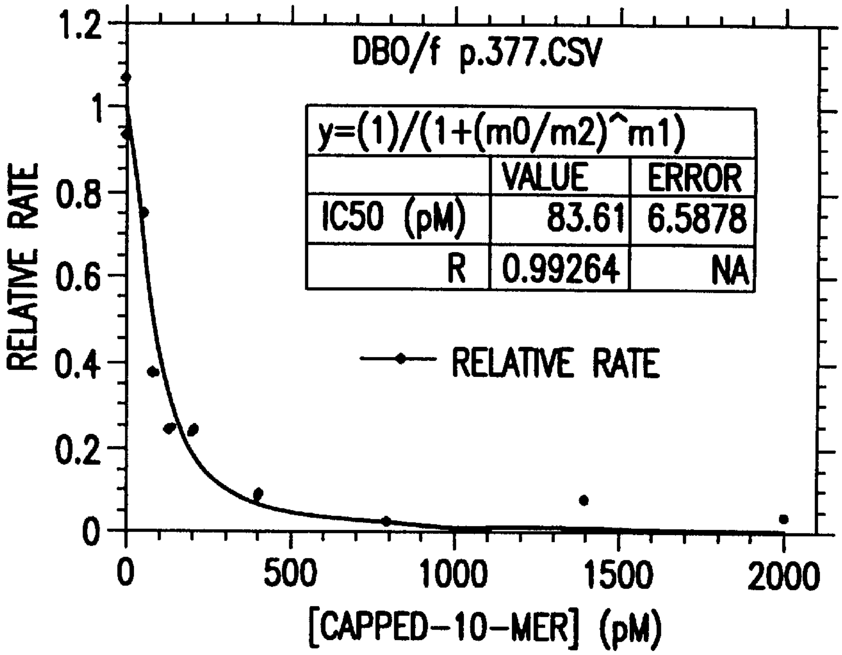
FIG. 1 is a graph of the Michaelis constant (Km) determined for a capped 19-mer substrate of influenza endonuclease, as further described in Examples 5 and 6.

The nucleotide is capped and a radiolabel is incorporated using guanyltransferase and alpha-$^{32}$P GTP. The resulting capped oligoribonucleotide:

$m^7G^{32}$pppG(2'-OMe)UUUUUAUUUUUAAUUUUC-3' (SEQ. ID. NO:2)

was purified by denaturing 20% PAGE and electroelution or by RP-HPLC. This substrate, and other derivatives listed below in Example 5, were used in various experiments to investigate the cleaving properties of influenza endonuclease. FIG. 1 shows the Km determined for the capped 19-mer SEQ.ID.NO.:2 shown above.

In another embodiment of this invention, a novel capped 10-mer was synthesized, based on the 5'-region of Brome Mosaic Virus (BMV):

$m^7$GpppG(2'-OMe)UAUUAAUA(3'-dA)-3'SEQ.ID.NO.:3.

Figure 2:
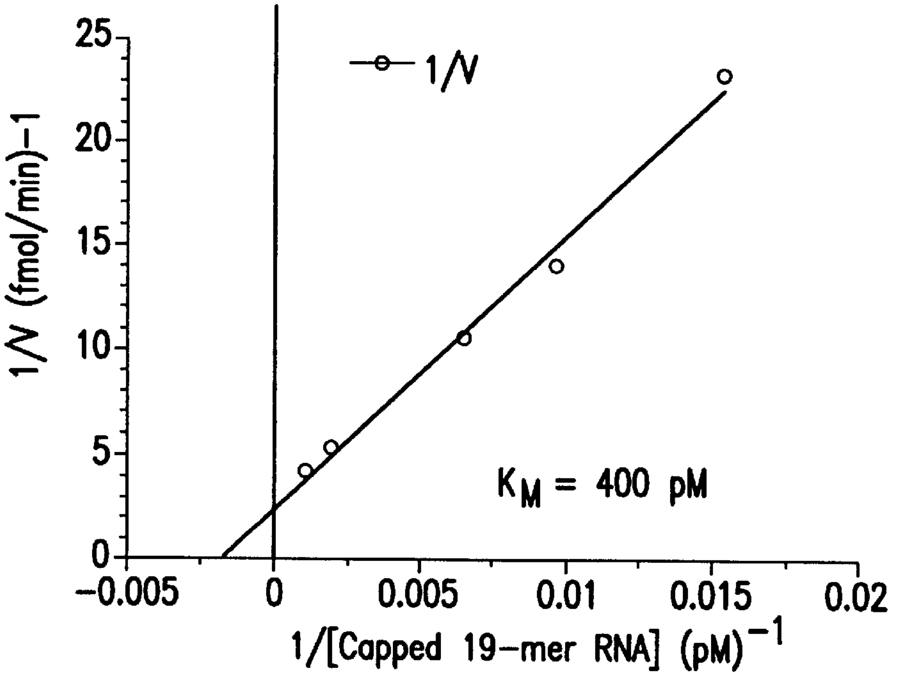
FIG. 2 is graph of the $IC_{50}$, the concentration of inhibitor that confers 50% inhibition under given conditions, determined for a capped 10-mer (SEQ.ID.NO.:3) inhibitor of influenza endonuclease, as further described in Examples 5 and 7.

The base sequence of this 10-mer was reported by Plotch et al, 1989, Cell 23:847–858 to be the shortest influenza endonuclease derived fragment from the cleavage of BMV RNA 4. The sequence reported by Plotch was then modified so that the 3'-adenosine was converted to a 3'-deoxyadenosine. This modification would result in an oligoribonucleotide that mimics the product of endonuclease cleaved BMV RNA but it would be "non-extendible" due to the absence of the 3'-hydroxyl on the terminal nucleoside. This compound was found to be an aptamer which is a potent inhibitor of influenza endonuclease; its $IC_{50}$ value was determined and is shown in FIG. 2. Thus another aspect of this invention is a method of treating or preventing an influenza infection in an animal susceptible to such an infection comprising administering to that animal a prophylactic or therapeutically effective amount of an aptamer which is an influenza endonuclease inhibitor, such as the above capped 10-mer.

The following capped RNA and capped RNA analoges were made following the processes of this invention. They were incubated with influenza endonuclease and were found to be substrates for the enzyme. The asterisk indicates the site of cleavage (or putative site).

pppG(2'-OMe)UUUUUAUUUUUA*AUUUUC-3' (SEQ.ID.NO.:4). This oligo (after being capped) is cleaved by influenza endonuclease between the two A's at positions 13–14 and has a Km of 400 pM.

pppG(2'-OMe)UUUUUAUUUUAG*CUUUUC-3' (SEQ.ID.NO.:5). This oligonucleotide is similar to SEQ.ID.NO.:4, above, except that it has a "GC" at positions 14–15.

pppG(2'-OMe)UUUUUAUUUUU(dA)*AUUUUC-3' (SEQ.ID.NO.:6). This oligo, which is an RNA/DNA mixed polymer is similar to SEQ.ID.NO.:5, above, except that it contains a 2'-deoxy-A at the putative cleavage site at position 13. This was synthesized to investigate whether the absence of the 2'-hydroxyl affected the ability of the influenza endonuclease to cleave the RNA.

pppG(2'-OMe)UUUUUAUUUUU(2'-FdA)*AUUUUC-3'(SEQ.ID.NO.:7). This is also a derivative of the AIMV substrate, but it has a 2'-deoxy-2'-fluoro-A at the putative site of cleavage. The presence of the 2'-FdA in the RNA was confirmed by limited base hydrolysis (of the $^{32}$P-labeled capped derivative) resulting in a nonspecific cleavage ladder observed after PAGE. The band corresponding to the cleavage between A13 and A14 was absent due to the lack of the 2'-OH at that position.

pppG(2'-OMe)UUUU(2'-FdU)AUUUU(2'-FdU)A*AUUUUC-3'(SEQ.ID.NO.:8). It was noticed that while influenza endonuclease specifically cleaves at positions 13–14, there was a small amount of non-specific cleavage occurring at position 6 and 12, possible due to some contaminating RNase A in the reaction mixture. This oligo, with a 2'-fluorine at positions 6 and 12, is resistant to RNase activity, and assays with influenza endonuclease show decreased background "noise". The presence of the two 2'-FdUs in the RNA was confirmed as described above for SEQ.ID.NO.:7.

pppG(2'-OMe)UUUU(2'-FdU)AUUUU(2'-FdU)(2'-FdA)*AUUUUC-3'(SEQ.ID.NO.:9). This is a derivative of the AIMV substrate, except that it contains a combination of two 2'-FdU sites and one 2'-FdA seen in the two oligoribonucleotides given above.

pppG(2'-OMe)UUUUUAUUUUUA*AUUUUC-(biotin)-3'(SEQ.ID.NO.:10). This oligo has the same primary structure as SEQ.ID.NO.:4, but has a biotin moiety attached so that the 3'-end of the oligoribonucleotide could be attached to a solid support.

pppA(2'-OMe)CACUUCUGG*UCCAGUCCG-3' (SEQ.ID.NO.:11). This oligo is based on the 5'-end of a-globin mRNA.

pppA(2'-OMe)CACUUGCUUUUG*ACACAA-3' (SEQ.ID.NO.:12). This oligo is based on the 5'-end of b-globin mRNA.

pppGUUUUUAUUUUUA*AUUUUC-3' (SEQ.ID.NO.:13) This oligonucleotide once capped would have a Cap 0 structure (i.e. there is no 2'-OMe at the penultimate base).

pppG(2'-OMe)U(2'-OMe) UUUUAUUUUUA*AUUUUC-3'(SEQ.ID.NO: 14). This oligonucleotide once capped would have a Cap 2 structure (i.e. a 2'-OMe at the penultimate base and one at the next 3'-base.

pppG(2'-OMe)UUUUUAUUUUUA“s”*AUUUUC-3' (SEQ.ID.NO.:15). This oligo contains a phosphorothioate moiety “s” at position 13. Substitution of one of the non-bridging oxygen atoms with the sulfur of the phosphate at the site of cleavage was made to inhibit the endonuclease activity of the influenza. Therefore, the capped version of this oligonucleotide analog may be a second type of aptamer against influenza endonuclease activity.

pppG(2'-OMe) UUUUUAUUUUU“s”A“s”*A“s”UUUUC-3' (SEQ.ID.NO.:16). This oligo is similar to SEQ.ID.NO.:15, above except it contains three phosphorothioate moieties at positions 12, 13, and 14. Influenza endonuclease is able to cleave capped RNAs 10–15 bases from the cap.

Other oligonucleotides which can be made using the methods of this invention are listed in Example 5, below. Thus another aspect of this invention are capped RNA and RNA analogs, and aptamers selected from the group consisting of: SEQ. ID. NOS. 1–21.

Pharmaceutically useful compositions comprising the capped RNA or analogs of this invention, and in particular those which are aptamers may be formulated according to known methods such as by the admixture of a pharmaceutically acceptable carrier. Examples of such carriers and methods of formulation may be found in Remington’s Pharmaceutical Sciences. To form a pharmaceutically acceptable composition suitable for effective administration, such compositions will contain an effective amount of the aptamer. Such compositions may contain admixtures of more than one aptamer.

Therapeutic or prophylactic compositions of the invention are administered to an individual in amounts sufficient to treat or prevent infections. The effective amount may vary according to a variety of factors such as the individual’s condition, weight, sex and age. Other factors include the mode of administration. Generally, the compositions will be administered in dosages ranging from about 1 mg to about 1 mg.

The pharmaceutical compositions may be provided to the individual by a variety of routes such as subcutaneously, topically, orally, mucosally, intravenously, intramuscularly, intranasally, transdermally, by suppository, and the like. Alternatively, the aptamer may be introduced into cells by microinjection, or by liposome encapsulation. Advantageously, aptamers of the present invention may be administered in a single daily dose, or the total daily dosage may be administered in several divided doses.

Aptamers may be particularly useful for the treatment of diseases where it is beneficial to inhibit influenza endonuclease activity, or prevent it from occurring. The pharmaceutical compositions are administered in therapeutically effective amounts, that is, in amounts sufficient to generate an influenza inhibiting response, or in prophylactically effective amounts, that is in amounts sufficient to prevent influenza endonuclease from acting on its substrate. The therapeutically effective amount and prophylactically effective amount may vary according to the type of aptamer. The pharmaceutical composition may be administered in single or multiple doses.

Aptamers synthesized or identified according to the methods disclosed herein may be used alone at appropriate dosages defined by routine testing in order to obtain optimal inhibition of the influenza endonuclease or its activity while minimizing any potential toxicity. In addition, co-administration or sequential administration of other agents may be desirable. For combination treatment with more than one active agent, where the active agents are in separate dosage formulations, the active agents can be administered concurrently, or they each can be administered at separately staggered times.

The dosage regimen utilizing the aptamers of the present invention is selected in accordance with a variety of factors including type, species, age, weight, sex and medical condition of the patient; the severity of the condition to be treated; the route of administration; the renal and hepatic function of the patient; and the particular aptamer employed. A physician of ordinary skill can readily determine and prescribe the effective amount of the aptamer required to prevent, counter or arrest the progress of the condition. Optimal precision in achieving concentrations of aptamer within the range that yields efficacy without toxicity requires a regimen based on the kinetics of the aptamer’s availability to target sites. This involves a consideration of the distribution, equilibrium, and elimination of the aptamer.

In the methods of the present invention, the aptamers herein described in detail can form the active ingredient, and are typically administered in admixture with suitable pharmaceutical diluents, excipients or carriers (collectively referred to herein as “carrier” materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following non-limiting Examples are presented to better illustrate the invention.

EXAMPLE 1

General Procedures:

The phosphitylating reagent 2-chloro-4H-1,3,2-benzodioxaphosphorin-4-one, tetra n-butylammonium fluoride (TABF, 1.0M solution in tetrahydrofuran) and N,-N-dimethylformamide (containing 4-E molecular sieves) were obtained from Fluka AG (Neu-Ulm, Germany). Pyridine and 1,4-dioxane (containing less than 0.01% $H_2O$) were obtained from E. Merck (Darmstadt, Germany) and stored over activated 4-E molecular sieves (E. Merck). Tri-n-butylamine, aqueous ammonium hydroxide (32%) and ethanol (pro analysis) were also obtained from E. Merck and used as supplied. HPLC grade acetonitrile and ethanol were purchased from Eppendorf/Biotronik (Hamburg, Germany).

Bis(tri-n-butylammonium)pyrophosphate was prepared according to the procedures of Ludwig and Eckstein, 1989, J. Org. Chem. 54:631–635, and Moffatt, 1964, Can. J. Chem 42:599–604, which are both hereby incorporated by reference. It was stored in aliquots under argon over activated E-4 molecular sieves at −20° C.

Monomeric 2'-tert-butyldimethylsilyl protected ribonucleotide phosphoramidites and synthesis columns, containing controlled pore glass (CPG) as the solid support with a ribonucleoside coupled to it, were obtained from Milligen/Biosearch (Eschborn, Germany). 2'-O-methyl ribonucleotide, 3'-deoxyphosphoramidite and biotin-CPG were purchased from GlenResearch (Sterling, USA). Preparation of 2'-FdA and 2'-FdU phosphoradimites was according to Olsen et al. 1991, Biochemistry 30:9735–9741; and Pieken et al 1991, Science 253:314–317, both of which are hereby incorporated by reference.

Analytical reversed-phase HPLC was performed on a column (4.6 mm×25 mm) containing 5 mm ODS-Hypersil (Shandon, Runcon, UK) using a DuPont 8800 instrument coupled to a DuPont 8800 UV detector.

EXAMPLE 2

Synthesis of Oligoribonucleotide 5'-Triphosphates

Automated oligonucleotide synthesis was carried out with an Applied Biosystems 380B DNA/RNA synthesizer on a 1 micromol scale with a final detritylation on the synthesizer using standard phosphoramidite chemistry as taught in Beuacage et al 1981 Tetrahedr. Letters 22:1859–1862 and Sinha et al, 1984 Nucleosides and Nucleotides 3:157-171 (both of which are incorporated by reference) with the following changes. A double coupling step was performed each with an incubation time of 10 min. In addition, the capping and oxidation steps were extended to 90 and 60 seconds respectively.

For the conversion of the CPG-bound oligonucleotides into the corresponding oligonucleotide triphosphates, essentially the method of Ludwig and Eckstein, 1988, (supra) was followed for the solution phase one pot synthesis of the nucleoside 5'-O-(1-thiotriphosphates). This same method was also used for the solid phase synthesis of 2'-O-methylribo-nucleoside 5'-triphosphates. (Guar et al, 1992 Tetrahed. Letters 33(23):2131–8, which is hereby incorporated by reference).

EXAMPLE 3

5'-Triphosphorylation of Oligoribonucleotides

After oligonucleotide synthesis was performed, the synthesis column was removed from the instrument and dried in high vacuum for 15 minutes. The column was then opened and the solid support was divided into two parts corresponding to the 0.2 mmol and the 0.8 mmol CPG-bound oligonucleotide, which were each transferred into a 2 ml glass vial. The 0.2 mmol aliquot was deprotected and purified as described below and used as a control. The 0.8 mmol aliquot containing glass vial was sealed with a rubber septum (which was punctured with a needle) and dried further in a high vacuum for 2 h at 35° C. The vial was flushed with argon by introducing the gas into the vacuum oven and the needle removed. The CPG was covered with anhydrous pyridine (50 ml) and anhydrous dioxane (150 ml) by injecting the solvents through the rubber septum using a glass syringe. A freshly prepared 0.5M solution of 2-chloro-4H-1,3,2-benzodioxaphosphorin-4-one in anhydrous dioxan (20 ml, 10 mmol) was then added with a glass syringe into the gently-vortexed suspension of the CPG-bound oligonucleotide. The reaction mixture, which was occasionally gently vortexed, was left in contact with the CPG for 15 min before a well-vortexed mixture of a 0.5M solution of bis (tri-n-butylammonium) pyrophosphate in DMF (150 ml, 75 mmol) and tri-n-butylamine (50 ml) was quickly injected into the vortexed suspension of the solid support. The major volume of the occasionally vortexed reaction mixture was carefully removed from the CPG after 15 min and subsequently replaced with an oxidation solution of 1% iodine in tetrahydrofuran/pyridine/water (80:10:10, v/v/v) (500 ml, 39 mmol). After 20 min, acetonitrile (1 ml) was added to the reaction mixture which was then vortexed and centrifuged before the supernatant was carefully removed and discarded. The wash process was repeated three times with acetonitrile (2 ml) and three times with ethanol (2 ml) to completely remove excess iodine and the other reagents before the oligoribonucleotide 5'-triphosphates were released from the solid support as mentioned below.

EXAMPLE 4

Deprotection and Purification of the Oligoribonucleotides and Oligoribonucleotide 5'-Triphosphates The oligoribonucleotides and oligoribonucleotide 5'-triphosphates were base-deprotected by incubation of the glass supports in a glass vial with 2 ml of $NH_3$:ethanol (3:1, v/v) at 55° C. for 14 h and further sugar deprotected and polyacrylamide gel purified as described by Heidenreich et al. 1994 J. Biol. Chem. 269:2131–2138 and Tuschl et al.

1993 Biochem. 32:11658–11668, both of which are hereby incorporated by reference. Crude products of the oligoribonucleotides and their corresponding oligoribonucleotide 5'-triphosphates were purified on the same gel for comparative analysis, revealing in general a slightly faster mobility for the triphosphorylated oligoribonucleotides.

The homogeneity of the oligoribonucleotides were analyzed by analytical reverse phase HPLC, injecting 0.1–0.2 A260 units of the products and employing a linear gradient of acetonitrile (1.4–14% in 20 min) in 50 mM of aqueous triethylammonium acetate buffer (pH 7.0) with a flow rate of 1.5 ml/min. Coinjection of control oligoribonucleotides with their corresponding oligoribonucleotide 5'-triphosphates revealed two peaks.

EXAMPLE 5

The following RNA substrates are made following the procedures set forth in Examples 2–4 above:

pppG(2'-OMe)UUUUUAUUUUUAAUUUUC-3' (SEQ.ID.NO.:4)

pppG(2'-OMe)UUUUUAUUUUAGCUUUUC-3' (SEQ.ID.NO.:5)

pppG(2'-OMe)UUUUUAUUUUU(dA)AUUUUC-3' (SEQ.ID.NO.:6)

pppG(2'-OMe)UUUUUAUUUUU(2'-FdA)AUUUUC-3' (SEQ.ID.NO.:7)

pppG(2'-OMe)UUUU(2'F-dU)AUUUU(2'F-dU) AAUUUUC-3'(SEQ.ID.NO.:8)

pppG(2'-OMe)UUUU(2'-FdU)AUUUU(2'-FdU)(2'-FdA) AUUUUC-3'(SEQ.ID.NO.:9)

pppG(2'-OMe)UUUUUAUUUUUAAUUUUC-(biotin)-3'(SEQ.ID.NO.:10)

pppA(2'-OMe)CACUUCUGGUCCAGUCCG-3' (SEQ.ID.NO.:11)

pppA(2'-OMe)CACUUGCUUUUGACACAA-3' (SEQ.ID.NO.:12)

pppGUUUUUAUUUUUAAUUUUC-3' (SEQ.ID.NO.:13)

pppG(2'-OMe)U(2'-OMe)UUUUAUUUUUAAUUUUC-3'(SEQ.ID.NO: 14)

pppG(2'-OMe)UUUUUAUUUUUA"s"AUUUUC-3' (SEQ.ID.NO.:15)

pppG(2'-OMe) UUUUUAUUUUU"s"A"s"A"s"UUUUC-3' (SEQ.ID.NO.:16)

pppA(2'-OMe)CACUUG-3'(SEQ.ID.NO.:17)

pppA(2'-OMe)CACUUCUG-3'(SEQ.ID.NO.:18)

pppG(2'-OMe)AAU-3'(SEQ.ID.NO.:19)

pppG(2'-OMe)UUU-3'(SEQ.ID.NO.:20)

pppG(2'-OMe)UAUUAAUA(3'dA)-3'(SEQ.ID.NO.:21)

EXAMPLE 6

Km of SEQ.ID.NO:2

Km Determination for Capped 19-mer ALMV substrate. Reactions were carried out at 31° C. in the presence of 50 mM TRIS-Cl, pH 7.8, 50 mM KCl, 1 mM DTT, 7.5 mM $MgCl_2$, approximately 3.3 $\mu$g ribonucleo-protein/ml and 32, 64, 103, 155, 516 or 1033 pM capped RNA. Reactions were initiated by the addition of capped RNA and 4.5 $\mu$l aliquots were quenched after 0.5, 1, 1.5 and 2 min by mixing with 3 $\mu$l of glycerol tolerent gel buffer (United States Biochemicals, Cleveland, Ohio) stop mix (GTGB-SM: 30 mM TRIS-Cl pH 9, 30 mM Taurine and 0.5 mM EDTA, 90% formamide, 0.1% (w/v) bromophenol blue and 0.1% (w/v) xylene cyanol FF). Reaction products were separated by running the samples on 64-well 8% sequencing gels using glycerol tolerent gel running buffer. The amount of cleavage of the substrate was quantified by standard Phosphorimager analysis. Lineweaver-Burk analysis of the data can be seen in FIG. 1.

EXAMPLE 7

Identification of an influenza endonuclease inhibitor

The following 10-mer was synthesized as described by the methods above: $m^7$GpppG(2'-OMe)UAUUAAUA(3'-dA)-3'(SEQ.ID.NO.:3) and was tested as an inhibitor of influenza endonuclease. $IC_{50}$ determination for Capped 10-mer. Purified viral ribonucleoprotein (3.3 mg protein/ml) was preincubated in a 20 ml volume at 25° C. for 30 min in the presence of 0, 0.05, 0.1, 0.15, 0.2, 0.4, 0.8, 1.4 or 2.0 nM $m^7$GpppG-(2'-OMe)UAUUAAUA(3'-dA)-3' (SEQ.ID.NO.:3) before the addition of 10 ml 1.2 nM of the capped 19-mer RNA $m^7$GpppG(2'-OMe)-UUUUUAUU-UUUAAUUUUC-3'(SEQ.ID.NO.:1). The final reaction buffer contained 100 mM Tris-Cl pH 8, 50 mM KCl, 5 mM DTT, 250 mM $MgCl_2$ and 0.55% glycerol. Aliquots (4.5 ml) of the reaction mixture were quenched after 0.5, 1.0, 1.5 and 2.0 min by mixing with 3 ml of glycerol tolerent gel buffer (United States Biochemicals, Cleveland, Ohio) stop mix (GTGB-SM:30 mM TRIS-Cl pH 9, 30 mM Taurine and 0.5 mM EDTA, 90% formamide, 0.1% (w/v) bromophenol blue and 0.1% (w/v) xylene cyanol FF). Reaction products were separated by running the samples on 64-well 8% sequencing gels using glycerol tolerent gel running buffer. The amount of cleavage of the substrate was quantified by standard Phosphorimager analysis. For determinations of $IC_{50}$ values, inhibitor saturation data were fit using a non-linear least-squares algorithm to Equation 1, $$Y = \frac{(1-a)\cdot[I_t]}{[I_t]+IC_{50}} \qquad (1)$$

where Y is the fraction activity inhibited, "a" is the residual activity at saturating concentrations of inhibitor, and $[I_t]$ is the total concentration of inhibitor. An $IC_{50}$ curve is shown in FIG. 2.

EXAMPLE 8

Equilibrium binding of an influenza endonuclease inhibitor

Purified ribonucleoprotein at a concentration of 2 mg/protein/ml was incubated at 25° C. for 30 min in a volume of 50 ml with various concentrations of $^{33}$P-labeled capped 10-mer (SEQ. ID. NO.:3) in a buffer containing 100 mM Tris-Cl pH 8.0, 50 mM KCl, 0.25 mM $MgCl_2$ and 5 mM DTT. 50 nM of 5'-triphosphorylated 10-mer (SEQ. ID. NO.:21) was included in all samples to displace nonspecific binding of the labeled capped 10-mer. Samples were filtered through 0.45 mm pore nitrocellulose membranes in a 96-well manifold (Schleicher and Schuell, Keene, N.H.) and were washed three times with 200 ml aliquots of buffer. Bound radioactivity was quantified using a Molecular Dynamics Phosphorimager.

Figure 3:
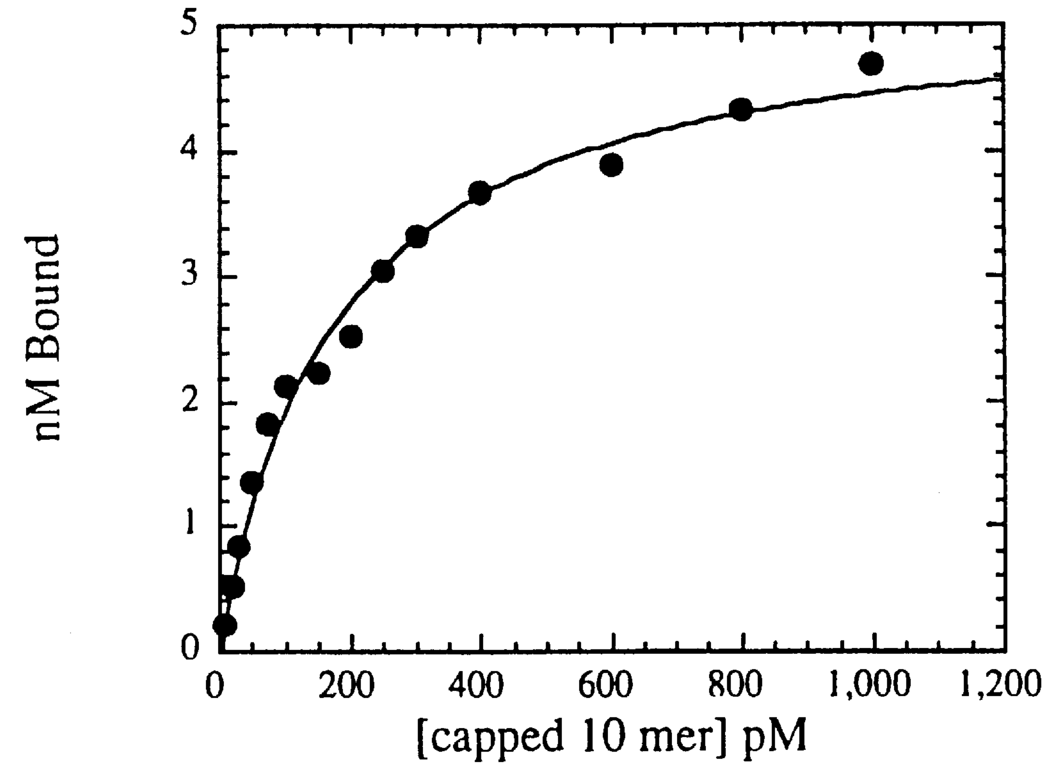
FIG. 3 shows an equilibrium titration of the binding of the capped 10-mer, as further described in Example 8.

Binding interactions of the capped 10-mer (SEQ.ID.NO.:3) with the low-pH treated influenza endonuclease preparation were characterized by a nitrocellulose filter retention assay. Under the conditions of this assay the capped 10-mer is only retained on the filter upon binding to the influenza endonuclease. FIG. 3 shows an equilibrium titration of the binding of the capped 10-mer. The data are consistent with a single class of non interacting binding sites. Nonlinear least-squares fitting returns values of $K_d$ of 170 pM and saturation amplitude of 5.2 nM. Only 10% of the binding of the labeled capped 10 mer is competed by up to 150 nM unlabeled 5'-triphosphorylated 10-mer of the same sequence. In contrast, 95% of the binding is displaced by competition with unlabeled capped 10 mer. Thus, the bulk of the capped 10-mer binding to the influenza endonuclease preparation is dependent on the presence of a 5'-cap and likely reflects direct binding to the endonuclease active site. The $K_d$ determined in the binding experiments is comparable to the $IC_{50}$ value of 83 pM for the same ligand determined in the enzymatic assays. The value of the saturation amplitude indicates that the concentration of endonuclease active sites is 50 pM under the conditions of the enzymatic assays, which is well below $K_d$ for the capped 10-mer binding or Km for the capped 19-mer substrate.

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:

( x i ) SEQUENCE DESCRIPTION: SEQ ID NO:1:

G U U U U U A U U U   U U A A U U U U C   1 9

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 2...2
( D ) OTHER INFORMATION:
( A ) NAME/KEY: Modified Base
( B ) LOCATION: 2...2
( D ) OTHER INFORMATION:

( x i ) SEQUENCE DESCRIPTION: SEQ ID NO:2:

G G U U U U U A U U   U U U A A U U U U C   2 0

( 2 ) INFORMATION FOR SEQ ID NO:3:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 2...2
( D ) OTHER INFORMATION:
( A ) NAME/KEY: Modified Base ( B ) LOCATION: 10...10
( D ) OTHER INFORMATION:
( A ) NAME/KEY: Modified Base
( B ) LOCATION: 2...2
( D ) OTHER INFORMATION:

( x i ) SEQUENCE DESCRIPTION: SEQ ID NO:3:

G G U A U U A A U A 1 0

( 2 ) INFORMATION FOR SEQ ID NO:4:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:

( x i ) SEQUENCE DESCRIPTION: SEQ ID NO:4:

G U U U U U A U U U U U A A U U U U C 1 9

( 2 ) INFORMATION FOR SEQ ID NO:5:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:

( x i ) SEQUENCE DESCRIPTION: SEQ ID NO:5:

G U U U U U A U U U U A G C U U U U C 1 9

( 2 ) INFORMATION FOR SEQ ID NO:6:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 13...13
( D ) OTHER INFORMATION:

( x i ) SEQUENCE DESCRIPTION: SEQ ID NO:6:

-continued

G U U U U U A U U U   U U A A U U U U C   1 9

( 2 ) INFORMATION FOR SEQ ID NO:7:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 13...13
( D ) OTHER INFORMATION:

( x i ) SEQUENCE DESCRIPTION: SEQ ID NO:7:

G U U U U U A U U U   U U A A U U U U C   1 9

( 2 ) INFORMATION FOR SEQ ID NO:8:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 6...6
( D ) OTHER INFORMATION:

( x i ) SEQUENCE DESCRIPTION: SEQ ID NO:8:

G U U U U U A U U U   U U A A U U U U C   1 9

( 2 ) INFORMATION FOR SEQ ID NO:9:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 6...6
( D ) OTHER INFORMATION:

( x i ) SEQUENCE DESCRIPTION: SEQ ID NO:9:

G U U U U U A U U U   U U A A U U U U C   1 9

( 2 ) INFORMATION FOR SEQ ID NO:10:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 19...19
( D ) OTHER INFORMATION:

( x i ) SEQUENCE DESCRIPTION: SEQ ID NO:10:

G U U U U U A U U U U U A A U U U U C 1 9

( 2 ) INFORMATION FOR SEQ ID NO:11:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:

( x i ) SEQUENCE DESCRIPTION: SEQ ID NO:11:

A C A C U U C U G G U C C A G U C C G 1 9

( 2 ) INFORMATION FOR SEQ ID NO:12:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:

( x i ) SEQUENCE DESCRIPTION: SEQ ID NO:12:

A C A C U U G C U U U U G A C A C A A 1 9

( 2 ) INFORMATION FOR SEQ ID NO:13:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:

( x i ) SEQUENCE DESCRIPTION: SEQ ID NO:13:

G U U U U U A U U U   U U A A U U U U C   1 9

( 2 ) INFORMATION FOR SEQ ID NO:14:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 2...2
( D ) OTHER INFORMATION:

( x i ) SEQUENCE DESCRIPTION: SEQ ID NO:14:

G U U U U U A U U U   U U A A U U U U C   1 9

( 2 ) INFORMATION FOR SEQ ID NO:15:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 13...13
( D ) OTHER INFORMATION:

( x i ) SEQUENCE DESCRIPTION: SEQ ID NO:15:

G U U U U U A U U U   U U A A U U U U C   1 9

( 2 ) INFORMATION FOR SEQ ID NO:16:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base -continued (B) LOCATION: 1...1
(D) OTHER INFORMATION:
(A) NAME/KEY: Modified Base
(B) LOCATION: 12...12
(D) OTHER INFORMATION:

(xi) SEQUENCE DESCRIPTION: SEQ ID NO:16:

GUUUUUAUUU UUAAUUUUC 19

(2) INFORMATION FOR SEQ ID NO:17:

(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: Genomic RNA (ix) FEATURE:
(A) NAME/KEY: Modified Base
(B) LOCATION: 1...1
(D) OTHER INFORMATION:
(A) NAME/KEY: Modified Base
(B) LOCATION: 1...1
(D) OTHER INFORMATION:

(xi) SEQUENCE DESCRIPTION: SEQ ID NO:17:

ACACUUG 7

(2) INFORMATION FOR SEQ ID NO:18:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: Genomic RNA (ix) FEATURE:
(A) NAME/KEY: Modified Base
(B) LOCATION: 1...1
(D) OTHER INFORMATION:
(A) NAME/KEY: Modified Base
(B) LOCATION: 1...1
(D) OTHER INFORMATION:

(xi) SEQUENCE DESCRIPTION: SEQ ID NO:18:

ACACUUCUG 9

(2) INFORMATION FOR SEQ ID NO:19:

(i) SEQUENCE CHARACTERISTICS:
(A) LENGTH: 4 base pairs
(B) TYPE: nucleic acid
(C) STRANDEDNESS: single
(D) TOPOLOGY: linear (ii) MOLECULE TYPE: Genomic RNA (ix) FEATURE:
(A) NAME/KEY: Modified Base
(B) LOCATION: 1...1
(D) OTHER INFORMATION:
(A) NAME/KEY: Modified Base
(B) LOCATION: 1...1
(D) OTHER INFORMATION:

(xi) SEQUENCE DESCRIPTION: SEQ ID NO:19:

GAAU 4

-continued ( 2 ) INFORMATION FOR SEQ ID NO:20:

( i ) SEQUENCE CHARACTERISTICS:
( A ) LENGTH: 4 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:

( x i ) SEQUENCE DESCRIPTION: SEQ ID NO:20:

G U U U 4

( 2 ) INFORMATION FOR SEQ ID NO:21:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: Genomic RNA ( i x ) FEATURE:
( A ) NAME/KEY: Modified Base
( B ) LOCATION: 1...1
( D ) OTHER INFORMATION:
( A ) NAME/KEY: Modified Base
( B ) LOCATION: 1...1
( D ) OTHER INFORMATION:
( A ) NAME/KEY: Modified Base
( B ) LOCATION: 10...10
( D ) OTHER INFORMATION:

( x i ) SEQUENCE DESCRIPTION: SEQ ID NO:21:

G U A U U A A U A A 1 0

What is claimed is:

1. A capped RNA or RNA analog selected from the group consisting of SEQ.ID.NOS: 1–21.

2. An oligonucleotide comprising the sequence of SEQ.ID.NO:3.

* * * * *